United States Patent [19]

Doonan

[11] Patent Number: 4,565,014

[45] Date of Patent: Jan. 21, 1986

[54] PROCESS FOR DRYING AMINOGUANIDINE BICARBONATE

[75] Inventor: David F. Doonan, Guilford, Conn.

[73] Assignee: Olin Corporation, Cheshire, Conn.

[21] Appl. No.: 613,698

[22] Filed: May 24, 1984

[51] Int. Cl.[4] .................................................. F26B 3/02
[52] U.S. Cl. ........................................ 34/36; 159/16.1;
159/47.1; 564/230
[58] Field of Search ............ 548/339; 159/47.1, 16 R,
159/22, 23; 34/36, 30; 564/230, 241, 232

[56] References Cited

U.S. PATENT DOCUMENTS

| | | | |
|---|---|---|---|
| 3,940,411 | 2/1976 | Asato et al. | 548/265 |
| 4,026,903 | 5/1977 | Asato et al. | 548/339 |
| 4,479,917 | 10/1984 | Rothgerm et al. | 252/175 |

FOREIGN PATENT DOCUMENTS 689191 2/1940 Fed. Rep. of Germany .
730331 10/1942 Fed. Rep. of Germany .

OTHER PUBLICATIONS

J. T. Thurston et al., "Aminogyanidonium Hydrogen Carbonate", Inorganic Systhesis, vol. III, pp. 45-47 (1950).

Olin Corporation Literature Search, NHTIS 81-217 (date May 29, 1981) and NHTIS 73-232 (date Sep. 4, 1973).

F. Kurzer and L. Godfrey, "The Synthesis of Aminoguanidine and Related Compounds", *Chemistry and Industry*, Sep. 8, 1962, pp. 1584-1595.

*Primary Examiner*—Larry I. Schwartz
*Attorney, Agent, or Firm*—William A. Simons; Thomas P. O'Day

[57] ABSTRACT

A process for drying a wet cake of aminoguanidine bicarbonate (AGB), which comprises subjecting the wet cake of aminoguanidine bicarbonate to drying temperatures from about 35° C. to about 95° C. under a carbon dioxide-containing atmosphere for a sufficient amount of time to form a dried aminoguanidine bicarbonate product which is substantially free of moisture.

10 Claims, No Drawings

PROCESS FOR DRYING AMINOGUANIDINE BICARBONATE

BACKGROUND OF THE INVENTION

1. Field of the Invention

This invention relates to a process for drying a wet cake of aminoguanidine bicarbonate under a $CO_2$-containing atmosphere at selected temperatures.

2. Brief Description of the Prior Art

Aminoguanidine bicarbonate (AGB) is a known chemical intermediate for many useful chemical products. For example, it may be converted into 3-amino-1,2,4-triazole, a known herbicide. AGB is a stable compound at ambient conditions whereas aminoguanidine is not stable under those conditions. Furthermore, AGB has advantageous properties as compared to other aminoguanidine salts. For example, it is insoluble in $H_2O$, which makes it easy to prepare in aqueous media.

Generally, AGB is made by reacting hydrazine or hydrazine hydrate with cyanamide or its salts (e.g. sodium or calcium) in the presence of an acid such as HCl, followed by adding a bicarbonate salt to the reaction mixture to precipitate out the AGB. The precipitated AGB is removed as a wet cake from the reaction mixture by filtration or centrifugation or the like. However, AGB is extremely heat sensitive when wet and discolors at temperatures as low as 35° C. under normal drying conditions such as drying under air or nitrogen. Furthermore, drying AGB at temperatures below about 35° C. results in long drying times and, in some cases, still results in undesirable amounts of residual moisture.

Accordingly, there is a need for an improved method of drying AGB whereby higher drying temperatures may be utilized without the undesirable discoloration.

It is an object of this invention to provide such an improved method for drying AGB.

BRIEF SUMMARY OF THE INVENTION

The present invention is, therefore, directed to a process for drying a wet cake of aminoguanidine bicarbonate (AGB), which comprises subjecting the wet cake of aminoguanidine bicarbonate to drying temperatures from about 35° C. to about 95° C. under a carbon dioxide-containing atmosphere for a sufficient amount of time to form a dried aminoguanidine bicarbonate product which is substantially free of moisture.

DETAILED DESCRIPTION

When aminoguanidine bicarbonate (AGB) is prepared by reacting hydrazine with cyanamide in the presence of HCl, followed by conversion to the bicarbonate salt with sodium bicarbonate, the following reactions (A) and (B) are thought to occur:

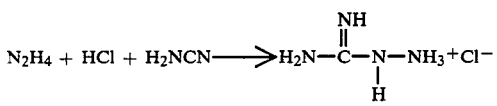

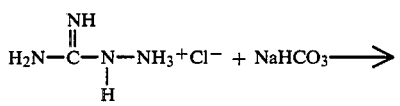

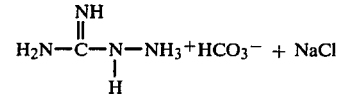

However, aminoguanidine bicarbonate is known to decompose to aminoguanidine, water and $CO_2$ according to the following reaction (C) in the presence of excessive heat:

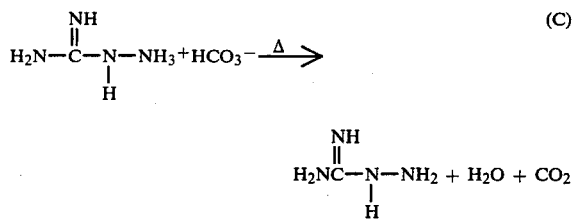

Also, aminoguanidine is reported to degrade to 3,6-diamino-1,2-dihydrotetrazine and ammonia according to reaction (D) as follows:

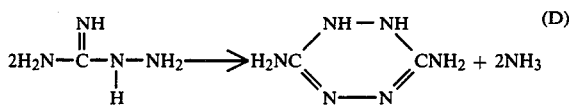

3,6-Diamino-1,2-dihydrotetrazine has a red color. It is thought that above reactions (C) and (D) describe the discoloration (and degradation) that occurs in the normal course of drying AGB as employed in the past.

Of course, AGB may be prepared by other synthesis methods, such as from sodium and calcium cyanamide. Also, other degradation products of AGB may be made which may cause the formation of an undesirable color in the product. Accordingly, the present invention encompasses all methods of making AGB where the product is recovered as a water-containing cake ready to be dried. Furthermore, the present invention is not to be limited as to avoiding any particular color-containing degradation product.

The term "wet cake" of AGB as employed in the present specification and claims refer to any water-containing AGB product which contains at least 5% by weight water. In most conventional processes, wet cakes of AGB from a filter press or centrifuge will contain from 15% to about 50% by weight water.

The wet cake of AGB may be dried at temperatures from about 35° C. to about 95° C. with any conventional drying means such as a shelf-type drying oven, a rotary drying oven or the like, as long as a $CO_2$-containing atmosphere is provided above the wet cake. It is believed that the $CO_2$-containing atmosphere suppresses degradation reactions such as shown in reactions (C) and (D), above. The term "$CO_2$-containing atmosphere" refers to any gaseous atmosphere which contains a sufficient amount of $CO_2$ to substantially retard or prevent the discoloration of aminoguanidine bicarbonate. A substantially pure (i.e. above 95% by volume) $CO_2$ atmosphere is preferred.

Preferably, the drying temperatures are from about 50° C. to about 90° C. The most preferable drying temperatures are from about 75° C. to about 85° C. At temperatures below about 35° C., even with a $CO_2$-containing atmosphere, the drying times are relatively long and uneconomical. At temperatures above about 95° C., small amounts of discoloration do occur even with a $CO_2$-containing atmosphere. It has been found that drying temperatures of about 75° C. to about 85° C. under a $CO_2$ atmosphere give relatively fast drying times without excessive heating costs and without degradation of the product.

The phrase "a dried aminoguanidine bicarbonate product which is substantially free of moisture" as employed herein refers to a dried AGB product which contains less than about 3% by weight $H_2O$. For most operations, it is preferred that the dried product contains less than about 2.5% by weight $H_2O$, more preferably, less than about 1% by weight water. The drying times will depend upon the moisture content in the wet cake, the drying temperature and the drying apparatus employed. Usually drying times will range from about 15 minutes to about 150 minutes or more.

The following example and comparison further illustrates the present invention. All parts and percentages are by weight unless explicitly stated otherwise.

EXAMPLE 1

A. Synthesis of Aminoguanidine Bicarbonate (AGB)

Hydrazine hydrate (64% hydrazine, 20 lbs, 0.4-mole) was charged to a 30-gal glass-lined reactor and hydrochloric acid (32.1%, 45.4 lbs, 0.4 lb-mole) was added to it with stirring and cooling over 30 min. The resulting hydrazine hydrochloride solution was heated to 80° C. and cyanamide (50%, 36 lbs, 0.43 lb-mole) was metered in over ~30 min in 5-lb increments while maintaining the reaction temperature at ~85° C. Reaction is exothermic; introduction of an initial 7-lb charge of $H_2NCN$ caused a temperature excursion from 80° to 103° C. during the first minute. Thereafter, with full reactor cooling, the temperature was maintained at 80°-85° C. range during remainder of addition. The mixture was stirred at 85° C. for 2 hrs, then cooled to 25° C. and the pH measured, which showed a value of 7.6. A slurry of sodium bicarbonate (35 lbs, 0.42 lb-mole) in 65 lbs of water was added all at once and the reaction was stirred overnight. The white solid product was isolated by centrifugation, washed with water (4 gal), then returned to the reactor and resuspended with 150 lbs fresh water. A final centrifugation gave 82 lbs of wet-cake which was dried in a vacuum oven at ~35° C. and 29 in Hg. Assay of the dried material showed 99% AGB, for an overall yield of 96% based on hydrazine charged.

B. Drying of Wet Centrifuge Cake Under $CO_2$ at 75° C.

A sample of AGB wet centrifuge cake (100 grams), 23.5% water, was placed on a watch glass in a 75° C. oven which was constantly purged with $CO_2$. After 2 hours, the sample was pure white and the moisture content was <0.5% by weight.

COMPARISON 1

Drying under Air at 75° C.

Another 100-g sample of AGB centrifuge cake was placed on a watch glass in a 75° C. oven, which was not purged of air. After 1 hour, the majority of the surface of the sample was a reddish color which indicated that surface portions of AGB decomposed.

COMPARISON 2

Drying under Nitrogen Atmosphere

Another 100-g sample of centrifuge cake was placed on a watch glass in a 75° C. oven, which was purged with nitrogen instead of $CO_2$. After 1 hour in the oven, the sample was observed to have reddish color on a majority of its surface. This again indicated that surface portions decomposed.

COMPARISON 3

Drying at Higher Temperature (100° C.)

A 100-g sample of centrifuge cake was placed on a watch glass in a 100° C. oven which was purged with $CO_2$. After 1 hour, the sample was dry but had a slight pink tinge indicating minor degradation.

What is claimed is:

1. A process for drying a wet cake of aminoguanidine bicarbonate comprising
    subjecting said wet cake of aminoguanidine bicarbonate to drying temperatures from about 35° C. to about 95° C. under a carbon dioxide-containing atmosphere for a sufficient amount of time to form a dried aminoguanidine bicarbonate product which is substantially free of moisture.
2. The process of claim 1 wherein said wet cake of aminoguanidine contains from about 15% to about 50% by weight water.
3. The process of claim 1 wherein said drying temperatures are from about 50° C. to about 90° C.
4. The process of claim 3 wherein said drying temperatures are from about 75° C. to about 85° C.
5. The process of claim 1 wherein said dried aminoguanidine bicarbonate contains less than about 2.5% by weight water.
6. The process of claim 5 wherein said dried aminoguanidine bicarbonate contains less than about 1% by weight water.
7. The process of claim 1 wherein said carbon dioxide-containing atmosphere is substantially pure $CO_2$.
8. A process for drying a wet cake of aminoguanidine bicarbonate containing from about 15% to about 50% by weight water comprising
    subjecting said wet cake of aminoguanidine to drying temperature from about 50° C. to about 90° C. under a substantially pure carbon dioxide atmosphere for a sufficient amount of time to form a dried aminoguanidine bicarbonate product containing less than about 2.5% by weight water.
9. The process of claim 8 wherein said dried aminoguanidine bicarbonate contains less than about 1% by weight water.
10. The process of claim 9 wherein said drying temperatures are from about 75° C. to about 85° C.

* * * * *